United States Patent [19]
McCarrell

[11]  4,345,599
[45]  Aug. 24, 1982

[54] TONSIL SNARE
[76] Inventor: Stuart G. McCarrell, 2204 N. Cleveland St., Chicago, Ill. 60614
[21] Appl. No.: 132,127
[22] Filed: Mar. 20, 1980
[51] Int. Cl.³ .................. A61B 17/00; A61B 17/36; A61B 1/72
[52] U.S. Cl. ............................ 128/320; 128/303.16; 128/309
[58] Field of Search ............... 128/303.16, 303.17, 128/309, 320, 305, 347

[56] References Cited
U.S. PATENT DOCUMENTS

| | | | |
|---|---|---|---|
| 1,722,474 | 7/1929 | Langbein | 128/320 |
| 1,731,069 | 10/1929 | Herman | 128/320 |
| 1,833,687 | 11/1931 | Neivert | 128/320 |
| 1,859,412 | 5/1932 | Smith | 128/320 |
| 2,115,298 | 4/1938 | Brown | 128/320 |
| 2,856,933 | 10/1958 | Hildebrand et al. | 128/305 |
| 3,897,787 | 8/1975 | Ikuno et al. | 128/303.17 |
| 3,923,063 | 12/1975 | Andrews et al. | 128/303.17 |

Primary Examiner—Kyle L. Howell
Assistant Examiner—C. W. Shedd
Attorney, Agent, or Firm—Hill, Van Santen, Steadman, Chiara & Simpson

[57] ABSTRACT

A snare instrument, useful for snaring tonsils, polyps and the like, has an elongate rod which is slidably and rotatably mounted in an elongate tube. The distal end of the rod is adapted for attachment of a wire snare loop which is collapsed about the snared organ as the elongate tube moves outwardly along the rod over the snare wire loop. The proximal ends of the tube and rod are provided with an operating handle in which a first plate, mounted on the tube, has a pair of holes therein for receiving the index and middle fingers, while a second plate is carried on the rod and has a hole therein for receiving the thumb of a user. In contrast to other snare instruments, the tube is moved upwardly along the rod upon a parting of the thumb and fingers, rather than on a closing of the thumb and fingers.

13 Claims, 4 Drawing Figures

TONSIL SNARE

BACKGROUND OF THE INVENTION

1. Field of the Invention

This invention relates to surgical instruments, and is more particularly concerned with snare instruments used for removal of protruding tissue, such as tonsils, polyps and the like.

2. Description of the Prior Art

Conventional snares operate so as to pull a wire loop, attached to a center rod, back into a sheath. For this purpose, the rod is provided with a pair of finger rings which are attached to the rod and a thumb ring which is attached to the tube. This structure has the advantage of providing the normal leverage of hand closure so that sufficient strength is available to accomplish removal of the tissue.

The disadvantage of conventional snares resides in the coupling between the finger rings and the rod. In one design the finger rings are attached to the rod through an elongate slot in the tube which permits extension of the distal end of the rod for threading of the wire loop and a travel upon closure of the hand which is sufficient to pull the rod sufficiently into the tube so that the loop is collapsed. In this context, it should be understood that the term "collapse" refers to decreasing the size of the loop an amount which is sufficient to cause separation of the tissue from the body.

In another conventional design, the tube is provided at the proximal end with a slide which is offset from the axis of the tube. The thumb loop is carried at the proximal end of the slide and the finger loops are slidably mounted on the slide with one loop attached to the proximal end of the rod.

When conventional snares, such as those discussed above, are also adapted for electro-surgery, additional structural elements must be provided to electrically connect the rod to an electro-surgical power supply, while at the same time electrically isolate the rod and power supply from the operating personnel.

Another disadvantage associated with conventional snares involves the attachment of the wire loop to the distal end of the rod. Conventionally, the distal end of the rod is provided with two transverse holes for receiving respective ends of the wires, the ends then being folded forward so that during movement of the rod into the tube the ends do not snag, reverse direction and disconnect from the rod. It is readily apparent that the distal end of the rod must be accessible to operating personnel for the purpose of threading. This is conventionally done in two ways: (1) additional forward travel of the rod is provided for exposure of the distal end; and (2) the rod is removed from the tube, threaded and reinserted, which may also involve disconnection of the finger loops and/or disassembly of the instrument.

SUMMARY OF THE INVENTION

The primary object of the present invention is to provide a new and improved snare instrument at a much lower expense than heretofore known.

Another object of the invention is to reassociate the hand and the instrument so that the fingers engage a portion of the handle carried by the tube and the thumb engages a portion of the handle carried by the rod, this reassociation changing the operating mode from the closure of the hand to the opening of the hand, and at the same time providing an effective increase in the cutting force and/or range of the normally weaker thumb-finger combination for cases of normal extension of the hand of the operating personnel.

The above objects are achieved, according to the present invention, by providing the proximal end of the tube with finger loops in the form of holes formed through a plate for receiving the index and middle fingers, and providing an edge on the plate immediately adjacent the middle finger hole for engagement by the ring finger. In addition, the plate may include an extension normal to that edge for additional engagement by the ring finger. This feature is essentially an additional finger ring and provides added leverage, when necessary, upon countering a particularly difficult cutting operation, such as fibrous tissue.

According to a particularly advantageous feature of the invention, the snare instrument is constructed to permit "prethreading" of the wire loop onto the distal end of a normally inaccessible portion of the center rod by providing a notch in the rearward facing edge of the first plate so that the second plate, when rotated 90° for example, is received in the notch for additional forward travel of the rod to expose the distal end of the rod for threading. With the loop threaded and the distal end of the rod moved rearwardly to the point where the second plate passes out of the notch, the point is reached at which the effective collapse of the wire loop may be accomplished with considerably less actual extension of the thumb and fingers, and at the point of greatest available separating force.

BRIEF DESCRIPTION OF THE DRAWING

Other objects, features and advantages of the invention, its organization, construction and operation will be best understood from the following detailed description, taken in conjunction with the accompanying drawing, on which.

DESCRIPTION OF THE PREFERRED EMBODIMENTS

Figure 1:
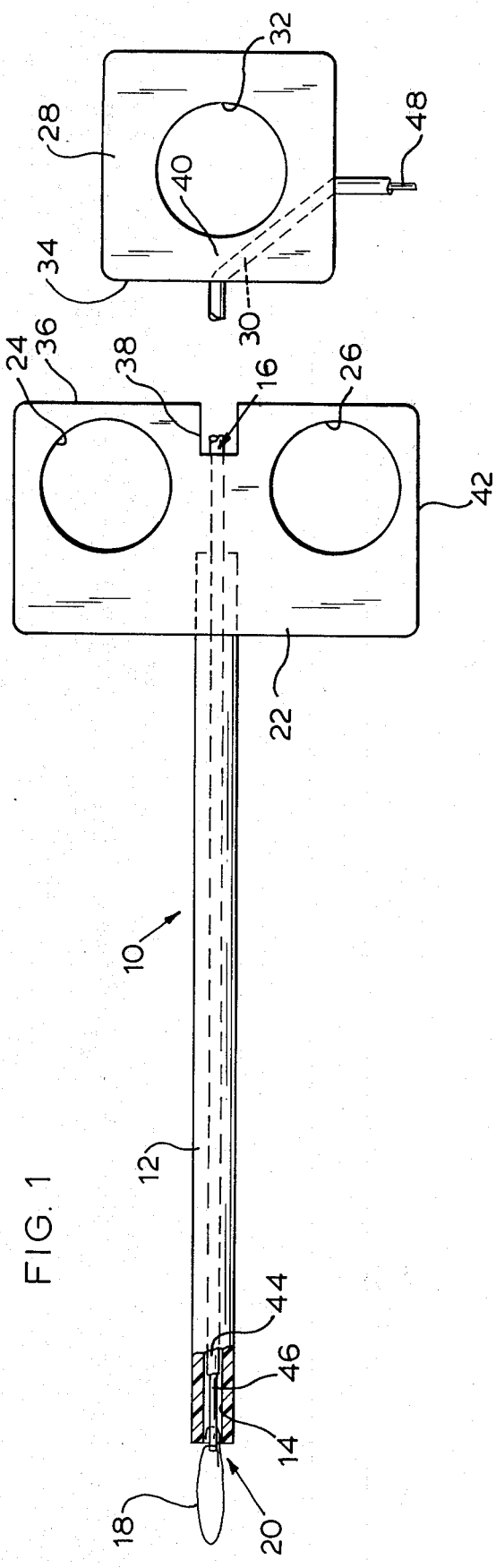
FIG. 1 is an elevational view, shown partially in fragmentary section, of a snare instrument constructed in accordance with the present invention.

Referring to FIG. 1, a snare instrument is generally illustrated at 10 as comprising a hollow elongate tube 12 which has a rod 16 mounted therein for axial movement and for rotational movement.

At the distal end of the rod is a wire loop 18 which is attached at 20 in a conventional manner.

The tube 12 carries a finger plate 22 at the proximal end thereof which includes a pair of finger holes 24 and 26.

The distal end of the rod 16 carries a thumb plate 28 which is attached to the rod 16 at 30.

Figure 4:
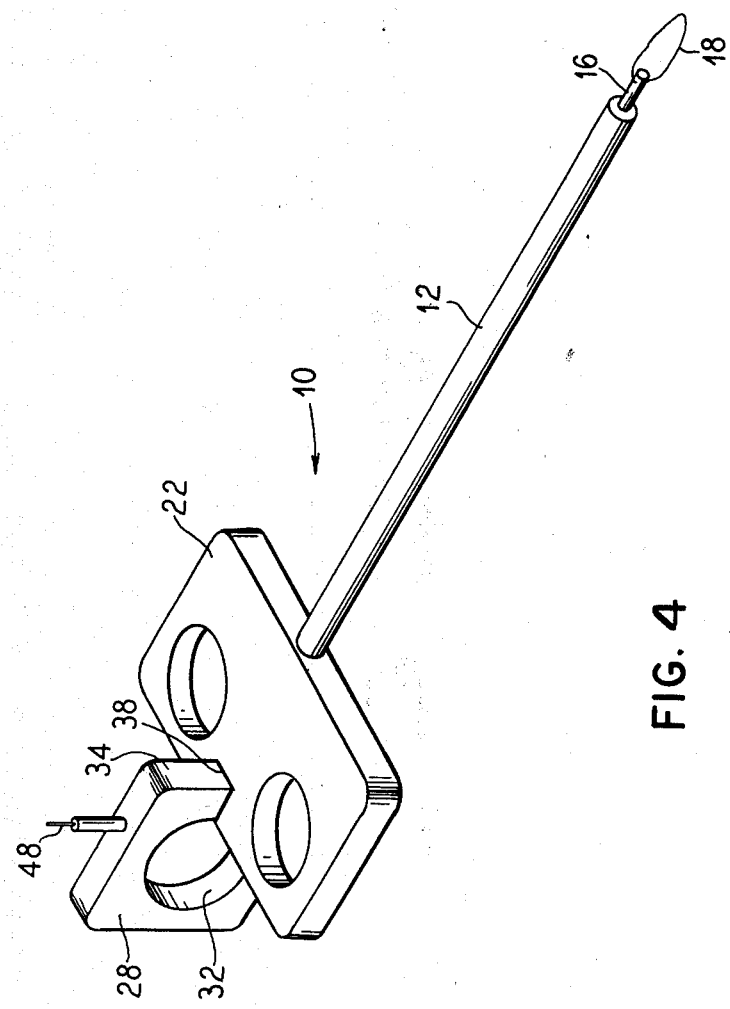
FIG. 4 is a perspective view of the snare instrument as it is conditioned for threading of a snare wire loop.

In the position of the rod and tube as illustrated at the distal end, the forward facing edge 34 of the finger plate 28 is in engagement with the rearward facing edge 36 of the finger plate 22, the plates 22 and 28 having been illustrated separated for clarity. In this position, the instrument is ready for operation at the point of maximum available force for separation of the thumb and fingers; however, it will be noted that the distal end of the rod is not accessible for threading. Therefore, the finger plate 22 is provided with a notch 38 which has a width which is at least slightly greater than the width of the thumb plate 28 to receive the thumb plate upon rotation of the thumb plate to a proper orientation, for example 90°, with respect to the finger plate 22 as best illustrated in FIG. 4. The additional forward distance of travel of the rod, for example one-half inch, exposes the distal end of the rod for threading. After threading, the thumb plate is withdrawn from the notch 38 and rotated to the operating position, that is essentially coplanar with the finger plate 22.

Thus far, the instrument described is usable for mechanical manipulative surgery. The instrument may be adapted for electro-surgery, however, by providing that the rod be constructed of an electrical conductor 46, covered by insulating material 44 and adapted at the proximal end with a terminal 48 for connection to an electro-surgical power supply.

Advantageously, all of the elements discussed above, with the exception of the wire loop 18 and the central conductor 46, when an electro-surgical instrument is desired, may be formed of plastic material and at much less expense than heretofore known.

A particular feature of the invention resides in the provision of an edge 42 on the finger plate 22 immediately adjacent the middle finger hole 26. When additional operating force is needed, this edge may be engaged by the ring finger to provide a frictional component which is additive to the leverage provided by the thumb, the index finger and the middle finger.

Figure 2:
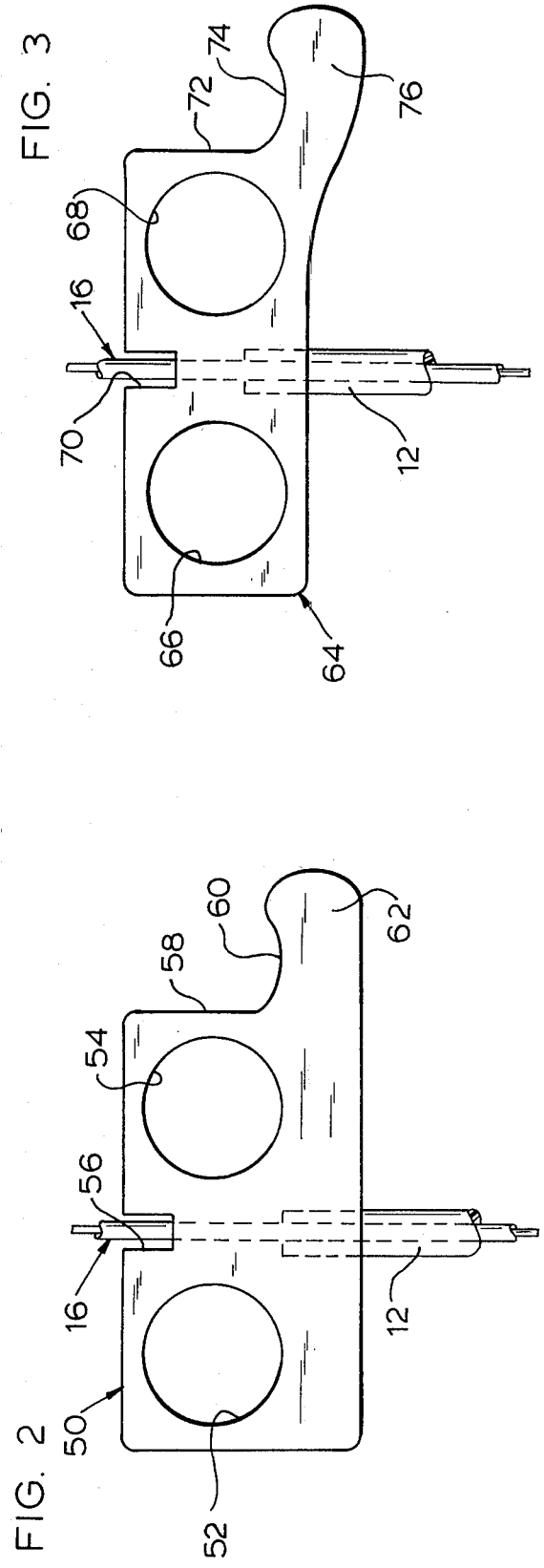
FIG. 2 is an elevational view of a portion of FIG. 1 having a different finger plate construction.

Referring to FIG. 2, a different structure is illustrated for a finger plate 50 which includes a pair of holes 52 and 54 for receiving the index and middle fingers and in FIG. 1. Also as in FIG. 1, an edge 58 has been provided adjacent the hole 54 for engagement by the ring finger, the edge 58 being further extended, so as to develop into an edge 60 which is substantially perpendicular to the edge 58, carried by a projection 62, also for engagement by the ring finger. The finger plate 50 is also provided with a notch 56 for the same purpose as the notch 38 in FIG. 1.

Figure 3:
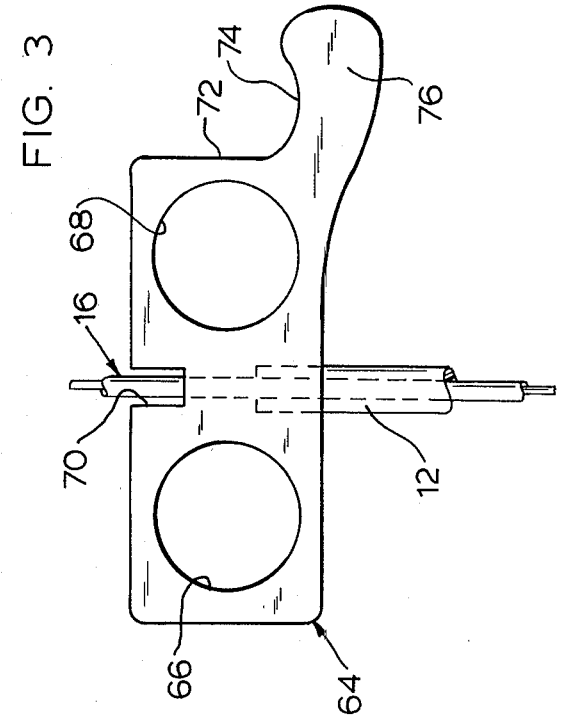
FIG. 3 is an elevational view of a portion of FIG. 1 having a finger plate of still another construction.

FIG. 3 illustrates a variation of the structure of FIG. 2 in which a finger plate 64 is provided with a pair of finger holes 66 and 68 and with a notch 70 for receiving the thumb plate. An edge 72 is provided adjacent the hole 68 for engagement by the ring finger and develops into an edge 74, carried by a projection 76, also for engagement by the ring finger. The difference between the structure of FIGS. 2 and 3 resides in the slight saving of material along the forward portion of the finger plate 64 as compared to the forward portion of the finger plate 50.

The snare instrument may be used, of course, for medical surgical applications, including veterinary applications; however, the instrument may also be employed as an elongation of one's reach in relatively inaccessible locations or environments to grip an object, as in the maintenance of aquariums and the like.

Although I have described my invention by reference to particular illustrated embodiments thereof, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. A snare instrument comprising: an elongate tube including a forward end and a rear end; finger means mounted at said rear end of said tube, said
    finger means comprising a first plate having a rear edge, first and second hole means defining respective first and second holes through said plate on opposite sides of said tube for receiving first and second fingers of the user, and notch means defining a notch in said rear edge;
    an elongate rod mounted in said tube for axial and rotary movement, said rod including a forward end adapted for attachment of a snare wire loop, and a rear end; and
    thumb means mounted on said rear end of said rod, said thumb means comprising a second plate having a forward edge, said second plate having a hole therein for receiving the thumb of a user,
    said rod having a predetermined length such that when said forward edge of said second plate engages said rear edge of said first plate said forward end of said rod is located within said tube,
    wherein relative rotation of said plates permits receipt of a portion of said second plate in said notch and permits forward movement of said first end of said rod out of said forward end of said elongate tube for attachment or detachment of the snare wire loop, and rearward movement of said rod in response to the parting of the thumb and fingers of the user causes said forward end of said tube to receive the snare wire loop and collapse the same.

2. The snare instrument of claim 1, wherein:
said tube and said plates are constructed of insulating material.

3. The snare instrument of claim 2, wherein:
said rod comprises an electrical conductor extending from said forward end to said thumb means and an electrical terminal at said thumb means for connection to an electrosurgical power supply.

4. The snare instrument of claim 1, wherein:
said first plate includes edge means for engagement by a third finger for applying increased force.

5. The snare instrument of claim 4, wherein:
said first plate includes a projection which carries at least a portion of said edge means.

6. The snare instrument of claim 1, wherein said finger means comprises:
an edge for engagement by a third finger for applying additional force.

7. The snare instrument of claim 6, wherein:
said edge extends generally parallel to the longitudinal axis of said rod.

8. The snare instrument of claim 6, wherein:
said edge extends generally perpendicular to the longitudinal axis of said rod.

9. The snare instrument of claim 1, wherein:
said finger means includes first and second edge portions for engagement by a third finger for applying additional force.

10. The snare instrument of claim 1, wherein:
said elongate rod includes an electrical conductor extending from said forward end to said thumb means, said electrical conductor including an electrical terminal at said thumb means for connection to an electrosurgical power supply.

11. A snare instrument comprising:

an elongate tube including a distal end and a proximal end;

means defining a pair of planar-oriented finger rings mounted at said proximal end for receiving, respectively, a finger of an operator;

means defining a notch between said finger rings opening outwardly from said proximal end;

a rod mounted in said tube for longitudinal and rotary movement, said rod including a distal end having attaching means for attaching a wire loop, and a proximal end including thumb means defining a thumb ring for receiving the thumb of an operator, said rod having a length such that said attaching means is positioned within the distal end of said tube when said finger rings and said thumb means are oriented coplanar and engaged, and positioned beyond said distal end of said tube when said thumb means is received in the notch.

12. The snare instrument of claim 11, wherein: said notch also opens transversely of the plane of said planar-oriented finger ring means and said thumb means is rotatable 90° to be received in said notch.

13. A snare instrument comprising:

an elongate tube including a forward end and a rear end;

an elongate rod slidably mounted within said elongate tube, said rod including a forward end, a rear end, means at said forward end for attaching a snare wire loop, and thumb means at said rear end for receiving a thumb; and finger means mounted on said elongate tube for receiving at least one finger, said elongate tube being axially slidable over said forward end of said rod to collapse the snare loop in response to a parting of the thumb and finger, said elongate rod being further rotatably mounted in said elongate tube, said finger means including a rear edge, said thumb means including a forward edge for engaging said rear edge when said elongate tube is at a first predetermined rearward position on said rod and at a first predetermined angular position on said rod, and said finger means including means defining a notch in said rear edge for receiving a portion of said thumb means when said elongate tube is at a second predetermined angular position on said elongate rod to permit movement of said tube to a second, predetermined, more rearward position on said rod so as to expose said forward end for attaching the snare wire loop.

* * * * *